United States Patent
Han et al.

(10) Patent No.: US 11,197,724 B2
(45) Date of Patent: Dec. 14, 2021

(54) MEDICAL PROBE

(71) Applicant: CUREXO, INC., Seoul (KR)

(72) Inventors: Yong Hee Han, Ulsan (KR); Jin Woong Kim, Ulsan (KR); Ji Sung Ko, Ulsan (KR); Jun Woo Park, Ulsan (KR)

(73) Assignee: CUREXO, INC., Seoul (KR)

( * ) Notice: Subject to any disclaimer, the term of this patent is extended or adjusted under 35 U.S.C. 154(b) by 218 days.

(21) Appl. No.: 16/326,620

(22) PCT Filed: Aug. 24, 2017

(86) PCT No.: PCT/KR2017/009268
§ 371 (c)(1),
(2) Date: Feb. 19, 2019

(87) PCT Pub. No.: WO2018/038555
PCT Pub. Date: Mar. 1, 2018

(65) Prior Publication Data
US 2020/0367973 A1 Nov. 26, 2020

(30) Foreign Application Priority Data
Aug. 24, 2016 (KR) .................. 10-2016-0107642

(51) Int. Cl.
*A61B 34/20* (2016.01)
*A61B 90/00* (2016.01)

(52) U.S. Cl.
CPC .............. *A61B 34/20* (2016.02); *A61B 90/06* (2016.02); *A61B 2034/2055* (2016.02); *A61B 2034/2072* (2016.02)

(58) Field of Classification Search
CPC ... A61B 2034/2055; A61B 34/20; A61B 5/00; A61B 90/06; A61B 2017/00477; A61B 2034/2072; A61B 2034/2068; A61B 2090/3983; G09B 23/30; G09B 23/28
See application file for complete search history.

(56) References Cited

U.S. PATENT DOCUMENTS

| | | | |
|---|---|---|---|
| 5,376,078 A | 12/1994 | Dinger, III et al. | |
| 5,429,641 A | 7/1995 | Gotfried | |
| 2009/0157088 A1 | 6/2009 | Mengato | |
| 2011/0257653 A1 | 10/2011 | Hughes et al. | |
| 2013/0096565 A1* | 4/2013 | Fritzinger | A61B 90/06 606/102 |
| 2015/0325151 A1* | 11/2015 | Tuchschmid | G09B 23/28 434/267 |

FOREIGN PATENT DOCUMENTS

| | | |
|---|---|---|
| CN | 1700887 A | 11/2005 |
| KR | 10-0599491 B1 | 7/2006 |
| KR | 10-0764815 B1 | 10/2007 |

* cited by examiner

*Primary Examiner* — Jon Eric C Morales
(74) *Attorney, Agent, or Firm* — Novick, Kim & Lee, PLLC; Jae Youn Kim; Jihun Kim

(57) ABSTRACT

Provided is a medical probe comprising a handle part to be held in hand, a position transmission part to be coupled to the hand part and to reflect or transmit a position signal to an optical tracking system (OTS), a main body to be coupled to one side of the handle part and to be positioned at an affected area of a patient, and a hook part to be coupled to the other side of the main body and to touch the affected area, wherein the hook part is coupled to the main body so as to have one angle of an acute angle, a right angle and an obtuse angle with respect to the main body.

6 Claims, 7 Drawing Sheets

II—II

I—I

MEDICAL PROBE

TECHNICAL FIELD

The present invention relates to a medical probe to obtain a position about an affected area of a patient by using image information from device such as an optical tracking system (OTS).

BACKGROUND ART

Generally, medical procedure is a medical technology for treating an affected area of a patient and comprises internal and surgical procedures. For example, there are various procedures such as an intervention procedure, ligament reconstruction surgery, joint replacement surgery, etc.

Such a medical procedure goes through a process to obtain an accurate position information about the affected area before performing a planned procedure for the affected area of the patient. The position information on the affected area of the patient is obtained through a probe and an optical tracking system (OTS). An operator matches the positions of the affected areas by using medical images pre-planned for the affected area and then saves the accurate position information, and the saved positions information is obtained by a spatial position transform matrix through a matching algorithm.

Meanwhile, the probe is to obtain the position information for the affected area of the patient to treat. The operator places the end of the probe through incision on the affected area of the patient to treat. At this time, the OTS receives a signal reflected or transmitted from a marker ball installed in the probe and thereby tracks the accurate position of the affected area to treat. Here, as the marker ball is positioned in parallel, the OTS receives and tracks the position of the probe accurately. Thus, the operator obtains the accurate position information for the affected area of the patient.

The conventional medical probe has a shape of straight rod such as a needle. Accordingly, the conventional medical probe has the following problems.

First, the shape of the conventional medical probe needs additional incision to obtain a wide range of spatial position information which is required for match.

Second, the straight shape of the conventional medical probe is used with lying obliquely on a curved part such as distal femoral and inner and outer sides of proximal tibial. Accordingly, the conventional medical probe is positioned perpendicular to the OTS, so that the OTS cannot track accurately the position of the marker ball to take a long time to match.

DETAILED DESCRIPTION OF THE INVENTION

Technical Challenge

The present invention is supposed to solve the above-mentioned problem and provide the medical probe which can obtain a wide range of the spatial position information without additional incision.

The present invention provides the medical probe which can obtain the position information in the curved part such as distal femoral and inner and outer sides of proximal tibial easily.

Solution to Problem

In order to solve the above-mentioned problems, the present invention can comprise the following configuration.

A medical probe according to the present invention comprises a handle part to be held in hand; a position transmission part to be coupled to the hand part and to reflect or transmit a position signal to an optical tracking system (OTS); a main body to be coupled to one side of the handle part and to be positioned at an affected area of a patient; and a hook part to be coupled to the other side of the main body and to touch the affected area, wherein the hook part is coupled to the main body so as to have one angle of an acute angle, a right angle and an obtuse angle to the main body.

In the medical probe according to the present invention, the main body is coupled to the handle part rotatably to change pointing direction of the hook part.

In the medical probe according to the present invention, the main body is formed in a curved shape so that a rotation axis of the main body and the end of the hook part might be positioned on the same line.

In the medical probe according to the present invention, the hook part is perpendicular to the rotation axis of the main body.

The medical probe according to the present invention further comprises a coupling part to couple the main body with the handle part, wherein the handle part comprises a penetration hole where the main body is inserted, wherein the main body comprises an insertion groove where the coupling part is inserted, wherein the coupling part is inserted into the insertion groove to be coupled to the main body so that the main body inserted through the penetration hole is prevented from being separated from the handle part.

In the medical probe according to the present invention, the handle part comprises a connection hole which is formed to be connected to the penetration hole, and the main body comprises a projection apparatus to be inserted into the connection hole and to be rotatably coupled to the handle part, and the projection apparatus is inserted into the connection hole and is formed in a polygonal shape to fix the main body.

The medical probe according to the present invention further comprises a light hole formed through the handle part.

In the medical probe according to the present invention, a plurality of the position transmitters is coupled to the handle part to be spaced apart each other.

The Effect of Invention

According to the present invention, the following effects are obtained.

The present invention does not need additional incision for a wide range of the spatial position information, so that it minimizes incision site of the patient, thereby reducing the patient's pain as well as shortening the patient's recovery time.

The present invention obtains the position information of the curved part such as distal femoral and inner and outer sides of proximal tibial easily to reduce the time for match.

BRIEF DESCRIPTION DRAWINGS

MODE FOR THE INVENTION

In the present invention, when elements of each of drawings are numbered reference numbers, it is noted that the same reference numbers are used to denote the same elements even if they are shown in other drawings.

Meanwhile, the meaning of terms described in the present invention should be understood as follows.

The singular expressions are to be understood as including plural expressions unless the context defines clearly differently, and terms like "the first", "the second" are used to distinguish one element from other element, the scope of the right should not be limited by these terms.

It should be understood that the terms like "comprise" or "have" do not preclude of one or more other features, numbers, steps, movements, elements, components, or the presence of combinations thereof or additional possibility.

It should be understood that the term of "at least one" comprises all possible combinations that can be presented from one or more related items. For example, "at least one of the first item, the second item and the third item" means combinations of all items that can be presented from two or more of the first item, the second item and the third item as well as the first item, the second item or the third item.

Hereinafter, a walking training apparatus according to the present invention will be described in detail with reference to attached drawings.

Figure 1:
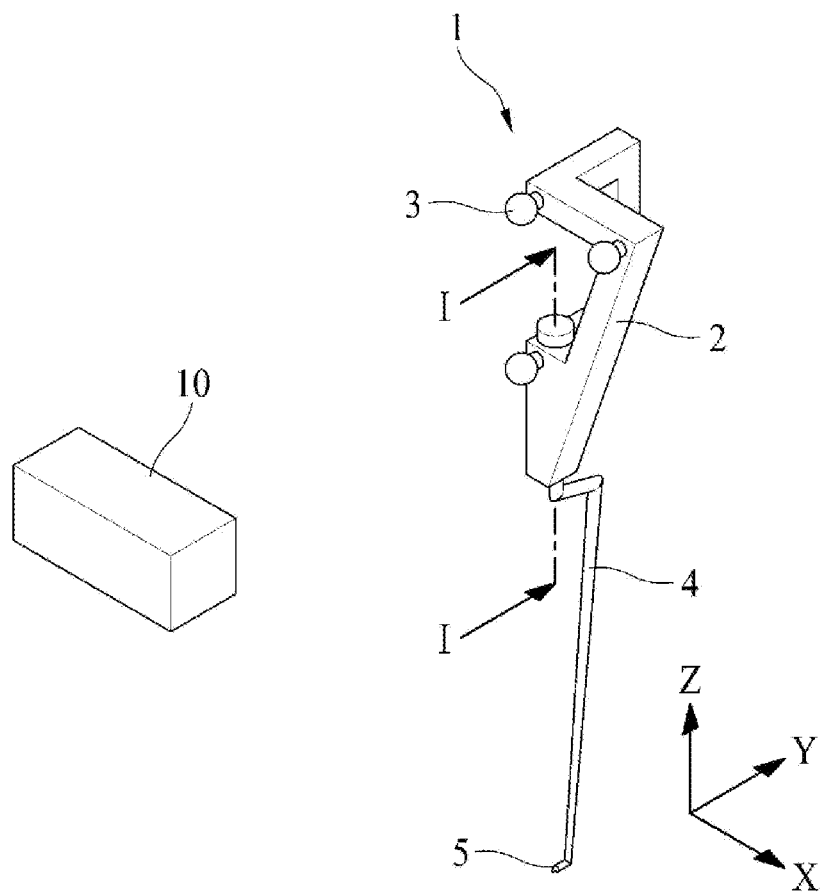
FIG. 1 is a schematic perspective view of a medical probe according to the present invention.
Figure 2:
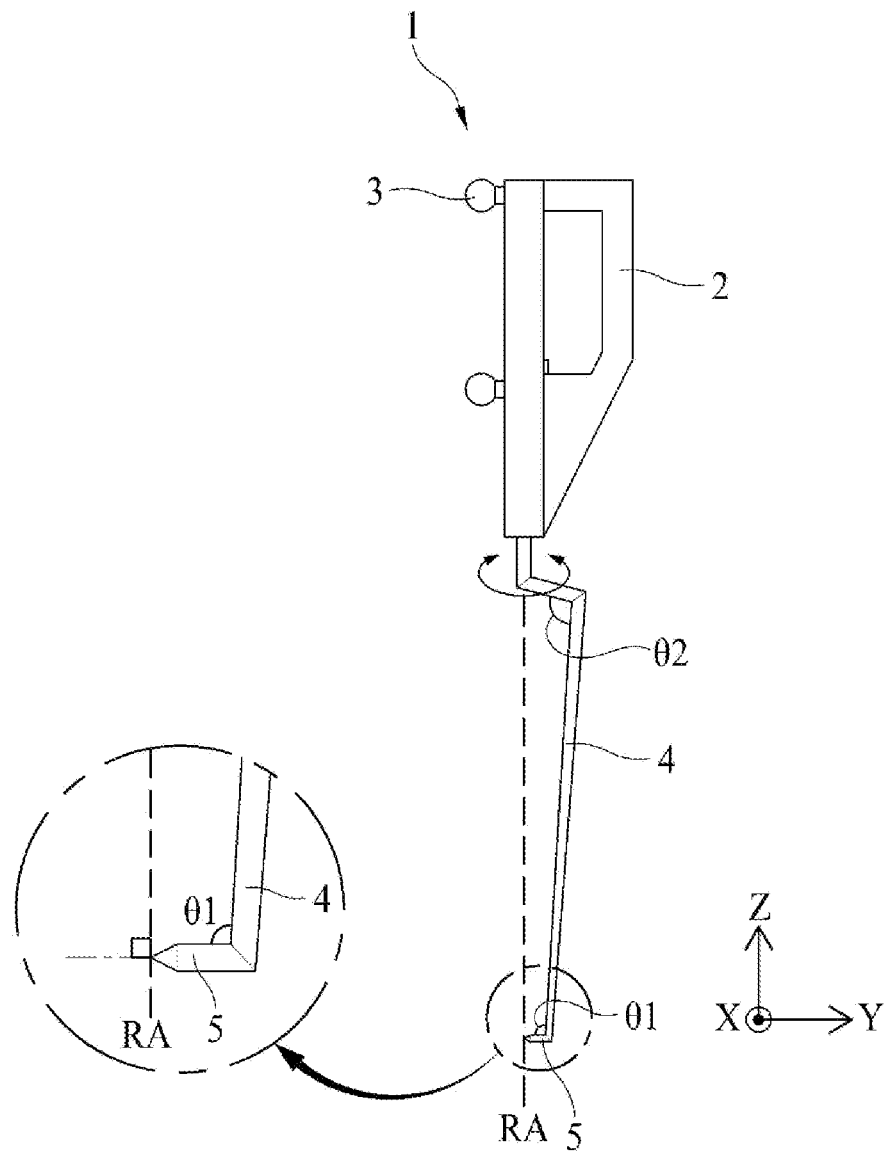
FIG. 2 is a schematic side sectional view for explaining the main body of the medical probe according to the present invention.
Figure 3:
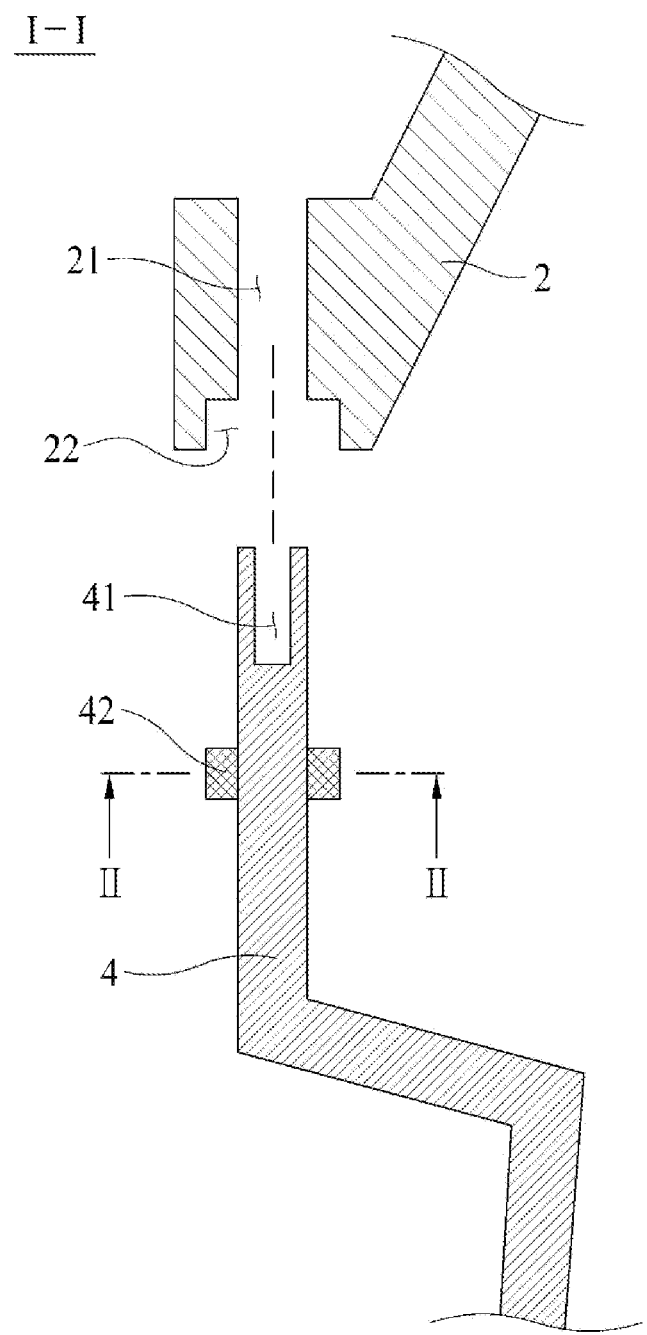
FIG. 3 is a schematic exploded sectional view along I-I line of FIG. 1 for explaining a penetration hole and an insertion groove of the medical probe according to the present invention.
Figure 4:
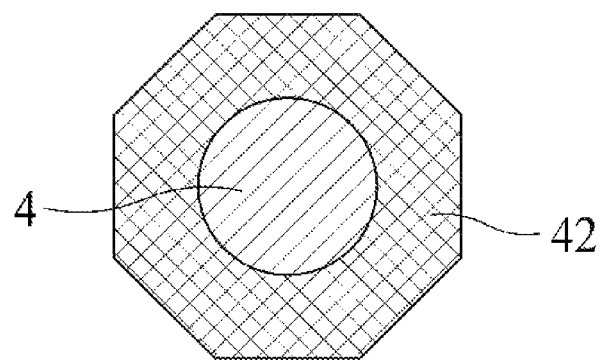
FIG. 4 is a schematic sectional view along II-II line of FIG. 3 for explaining a projection apparatus of the medical probe according to the present invention.
Figure 5:
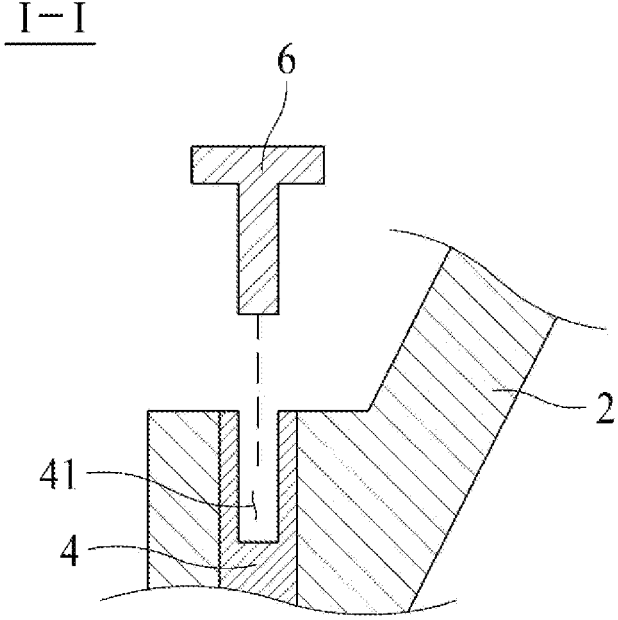
FIG. 5 is a schematic exploded sectional view along I-I line of FIG. 1 for explaining a coupling part of the medical probe according to the present invention.
Figure 6:
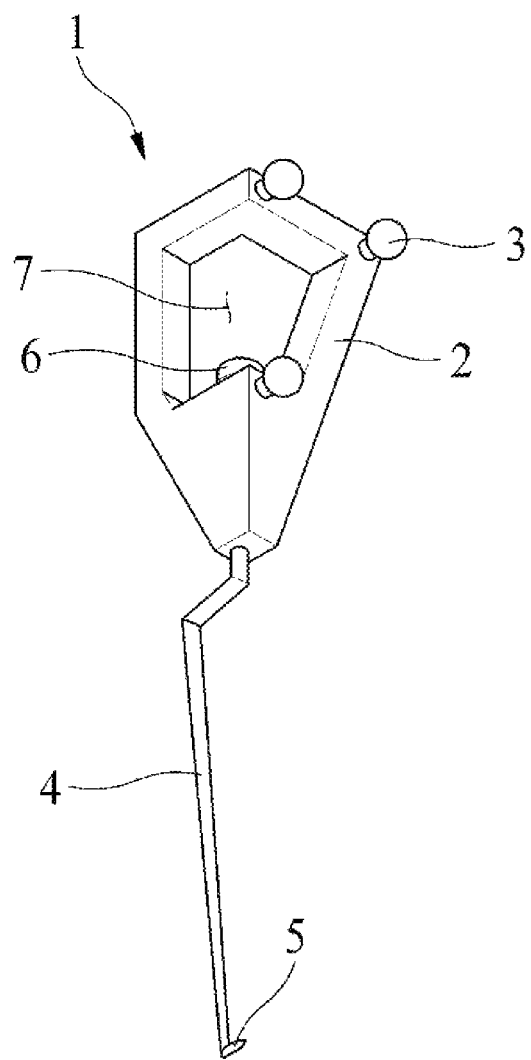
FIG. 6 is a schematic perspective view for explaining a light hole of the medical probe according to the present invention.
Figure 7:
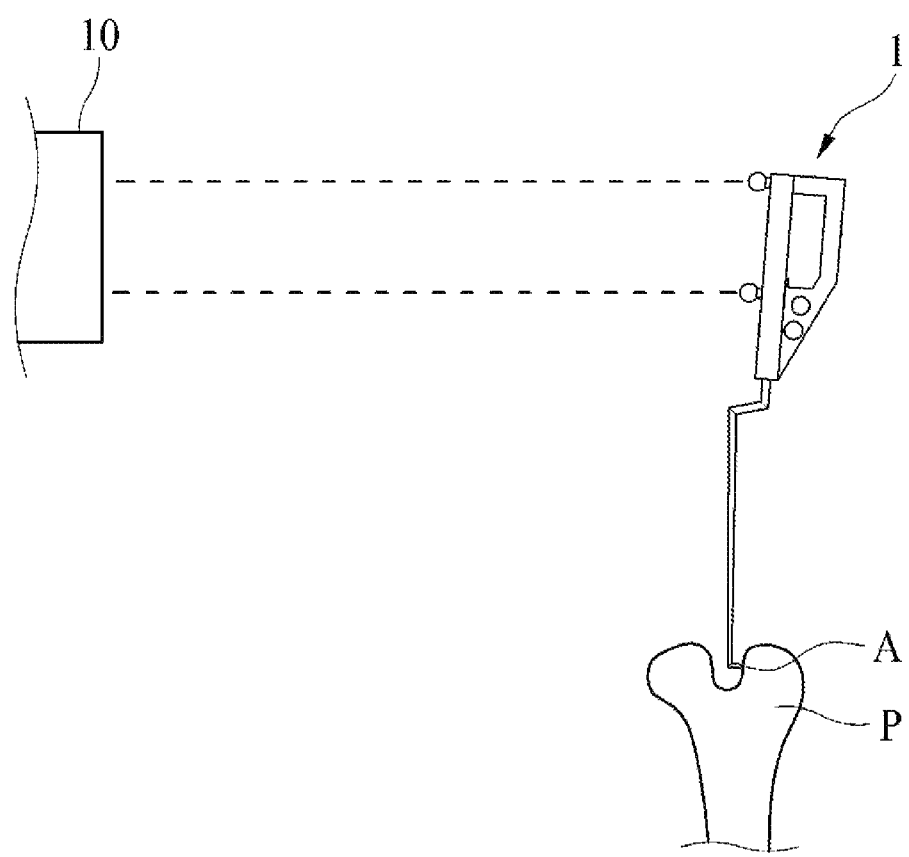
FIG. 7 and FIG. 8 are schematic operation state views of the medical probe according to the present invention.
Figure 8:
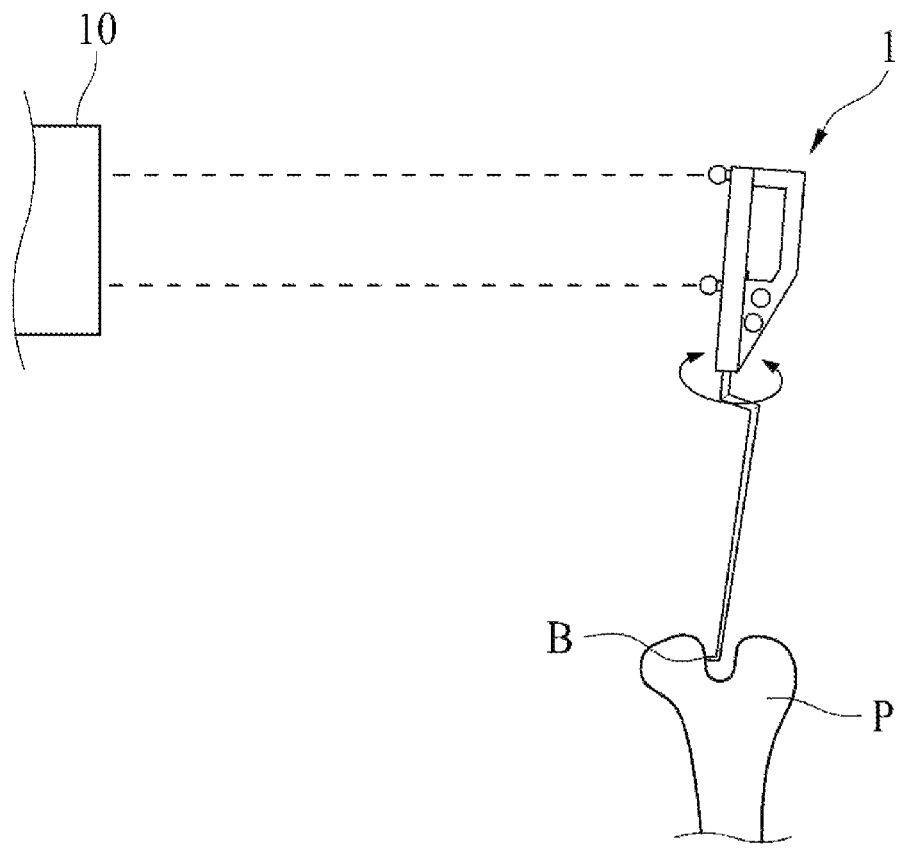

FIG. 1 is a schematic perspective view of a medical probe according to the present invention, FIG. 2 is a schematic side sectional view for explaining the main body of the medical probe according to the present invention, FIG. 3 is a schematic exploded sectional view along I-I line of FIG. 1 for explaining a penetration hole and an insertion groove of the medical probe according to the present invention, FIG. 4 is a schematic sectional view along II-II line of FIG. 3 for explaining a projection apparatus of the medical probe according to the present invention, FIG. 5 is a schematic exploded sectional view along I-I line of FIG. 1 for explaining a coupling part of the medical probe according to the present invention, FIG. 6 is a schematic perspective view for explaining a light hole of the medical probe according to the present invention, FIG. 7 and FIG. 8 are schematic operation state views of the medical probe according to the present invention.

Referring to FIGS. 1 to 8, the medical probe 1 according to the present invention is to obtain accurate procedure position for the curved affected area such as distal femoral and inner and outer sides of proximal tibial. Also, the medical probe 1 according to the present invention may obtain a wide range of spatial position information with minimum incision. The medical probe 1 according to the present invention is put in pre-planned position and then the accurate position image information is gotten with the OTS.

For this, the medical probe 1 according to the present invention comprises the handle part 2, the position transmission part 3, the main body 4, and the hook part 5.

The OTS 10 (shown in FIG. 1) is a device to detect and track spatial position and direction of an object, such as a surgical tool like a probe 1 or patient's affected area. The OTS 10 may comprise a processor that tracks signals reflected or transmitted by the position transmission part 3 attached in the handle part 2, calculates three-dimensional coordinate of the position transmission part 3, compares it with a pre-stored three-dimensional coordinate of the position transmission part 3, and then calculates spatial position and direction of the object. The OTS 10 may be installed spaced apart from the affected area A (shown in FIG. 7) in the body of the patient P (shown in FIG. 7). The OTS 10 may receive position signals from the position transmission part 3 easier as the position transmission part 3 is positioned in parallel, so that it obtains the accurate position information of the probe 1. The body of the patient P may be a distal femoral and inner and outer sides of proximal tibial where the affected area A is positioned. The probe 1 is inserted into incision through skin to indicate the affected area A.

Hereinafter, the handle part 2, the position transmission part 3, the main body 4 and the hook part 5 will be described in detail with reference to attached drawings.

Referring to FIG. 1 to FIG. 8, the handle part 2 is for an operator to hold by hand. The handle part 2 is positioned in an upper side of the probe 1 along a Z-axis direction (shown in FIG. 1). The main body 4 is below the handle part 2. Accordingly, the handle part 2 is spaced apart from the affected area as the main body 4 is inserted into the patient to contact the affected area A. The handle part 2 may be formed in a polygonal shape which becomes smaller from the upper side to the lower side. However, it is not limited to this and it has other forms such as a rectangle or a circle shape if the operator holds it easily.

The position transmission part 3 is installed at one side of the handle part 2. The one side of the handle part 2 where the position transmission part 3 is coupled, is made to direct toward the OTS 10 by the operator. In this case, the OTS 10 easily receives signals reflected or transmitted from the position transmission part 3, so that it can track accurately the position of the probe 1. The handle part 2 may be made from plastic material for light weight, but it could be other materials. The handle part 2 may comprise the penetration hole 21 and the connection hole 22.

The position transmission part 3 reflects or transmits position signals to the OTS 10. The position transmission part 3 may be coupled to the one side of the handle 2, and there may be a plurality of the position transmission part 3 spaced apart from each other. For example, three position transmission parts 3 is installed at the one side of the handle part 2 with spaced apart from each other. Also, the three position transmission parts 3 is located at a vertex of a right triangle respectively in the one side of the handle part 2, but it is not limited to this. The OTS 10 receives and triangulates the position signals reflected or transmitted by the three position transmission parts 3 to obtain the position of the handle part 2.

In this case, the main body 4 and the hook part 4 are coupled with the handle part 2, and thus the operator can know the indicative position of the hook part 5 from the position of the handle part 2. The position transmission part 3 may be a marker ball. As shown in FIG. 1, the OTS 10 may easily receive the position signal reflected or transmitted from the position transmission part 3 as the marker ball is located in parallel. To locate the marker ball in parallel with the OTS 10 means the state that an imaginary plane formed by a plurality of the position transmission parts 3 is in parallel with one side of the OTS 10. As the imaginary plane and the one side of the OTS 10 are perpendicular to each other, the OTS 10 may not receive positions for the position transmission part 3 accurately.

The main body 4 is to be located in the affected area A of the patient. For example, the main body 4 may be partly or all positioned in the affected area A by contacting with the patient's skin or be inserted into the patient's skin through an incision. The main body 4 may be coupled to one side in the handle part 2. For example, the main body 4 and the handle part 2 are made to be on a line. The main body 4 is inserted into the penetration hole 21 formed in the handle part 2. The penetration hole 21 is formed through the handle part 2 to provide the insertion of a part of the main body 4. The main body 4 inserted into the penetration hole 21 may be coupled to the main body 4 by a coupling part 6 which is described in below. The main body 4 may be formed in a straight stick shape, but is not limited to this. Also, it may be formed in a curved shape. The other side of the main body 4 is coupled to the hook part 5. The main body 4 may comprise the insertion groove 41 and the projection apparatus 42.

The hook part 5 is to contact to the affected area A. One side of the hook part 5 may be coupled to the main body 4 at one angle among an acute angle, a right angle and an obtuse angle. The hook part 5 is formed in a cylinder shape and have a sharp tip at the other side. However, it is not limited to this and it may be formed in other shapes if it indicates the affected area A of the patient body P accurately. The other side of the hook part 5 may be the end of the hook part 5. Accordingly, the hook part 5 may be projected in a Y-axis direction (shown in FIG. 2) from the main body 4. A length of the hook part 5 may be 5 mm, but is not limited to this. The hook part 5 may be made separately to be coupled to the main body 4, and alternatively it may be made integrally with the main body 4 by injecting molding or a metal molding. In this case, the hook part 5 may have a first angle $\theta 1$ to the main body 4. The hook part 5 may be made from the same material with the main body 4, not excluding different materials. Accordingly, due to the hook part 5 formed at the first angle $\theta 1$ to the main body 4 the medical probe 1 according to the present invention may indicate the position of curved object better than the conventional probe of straight shape. Therefore, the medical probe 1 according to the present invention reduces the time required for positioning at the planned procedure position accurately, thereby reducing the matching time and the whole procedure time.

The main body 4 may be coupled to the handle part 2 rotatably to change the direction which the hook part 5 points out. A part of the main body 4 connected to the handle part 2 rotates in a clockwise or counterclockwise direction on a rotation axis (RA, shown in FIG. 2) with keeping the coupling to the handle part 2 and thus the pointing direction of the hook part 5 is changed. The pointing direction of the hook part 5 means the direction which the end of the hook part 5 points out. The main body 4 may rotates with spaced apart from the handle part 2 to change the pointing direction of the hook part 5 and then be coupled to the handle part 2. Accordingly, rotation of the main body changes the pointing direction of the hook part 5. In this case, the handle part 2 does not rotate, so it keeps in the direction toward the OTS 10 continuously. Accordingly, the medical probe 1 according to the present invention may change the pointing direction of the hook part 5 by rotating the main body 4, so that the hook part 5 may point out another affected area (B, shown in FIG. 8) at another position without additional incision. Therefore, the medical probe according to the present invention may obtain a wide of spatial position information required to match without additional incision. Also, the medical probe 1 according to the present invention does not have to rotate the handle part 2 directing toward the OTS 10 and thus may receive position signals easily from the position transmission part 3 and obtain the accurate position of the affected area A. Although not shown, the medical probe 1 according to the present invention may rotate the handle part 2 on the main body 4 with keeping the position of the main body 4 to direct toward the OTS 10 when the position of the OTS 10 is changed.

The main body 4 is rotatable to the handle part 2 but it may be fixed by the projection apparatus 42 to prevent the rotation. The projection apparatus 42 has a polygonal shape. The projection apparatus 42 may be formed integrally with the main body or formed separately to be coupled to the main body 4. The projection apparatus 42 is inserted into the connection hole 22 and is supported by the handle part 2, so it prevents the main body 4 from rotating for the handle part 2. The connection hole 22 is formed in the handle part 2 to connect with the penetration hole 21. The connection hole 22 may be bigger than the penetration hole 21. The connection hole 22 may have the same shape with projection apparatus 42 to permit the insertion of the projection apparatus 42. For example, the projection apparatus 42 and the connection hole 22 may have an octagonal shape. As the projection apparatus 42 has the octagonal shape, the main body 4 may rotate by 45 degrees. That is, the projection apparatus 42 may limit the fine rotation of the main body 4. The projection apparatus 42 may have the polygonal shape over octagon, so that the main body 4 rotates at an angle smaller than 45 degrees. Accordingly, the medical probe 1 according to the present invention may finely rotate the main body 4 for the handle part 2, thereby indicating the planned procedure position more accurately.

The main body 4 may be formed in a curved shape so the end of the hook part 5 and the rotation axis of the main body 4 (RA) are on a line. For example, the main body 4 may be curved to have a second angle $\theta 2$. The end of the hook part 5 means the other side opposite to one side of the hook part 5 coupled to the main body 4. The end of the hook part 5 may indicate the accurate affected area A to treat actually through the process of matching with the procedure position pre-planned by the operator. The main body 4 may be formed in a curved shape so that the hook part 5 may avoid the projected part above the affected area A and indicate accurately the affected area A. The first angle $\theta 1$ and the second angle $\theta 2$ may be changed depending on a length of the main body 4 formed in the Z-axis direction (shown in FIG. 2). In this case, the hook part 5 may be perpendicular to the rotation axis RA of the main body 4. Accordingly, the medical probe 1 according to the present invention may let the end of the hook part 5 keep a constant coordinate value in the space even if the main body 4 rotates on the rotation axis RA. Therefore, the medical probe 1 according to the present invention may reduce more and more time required for matching with the planned procedure position.

The medical probe 1 according to the present invention may further comprise the coupling part 6.

The coupling part 6 is to couple the main body 4 to the handle part 2. For example, the coupling part 5 may be a bolt. The coupling part 6 may be inserted into the insertion groove 41 formed in the main body 4 if the main body 4 is inserted through the penetration hole 21. The insertion groove 4 is a groove dented toward the inside of the main body 4 so that the coupling part 6 is inserted. The insertion groove 41 may be formed in one side of the main body 4. The coupling part 6 may be inserted into the insertion groove 41 and coupled to the main body 4 by one of screw coupling or press coupling. Accordingly, the coupling part 6 may couple the main body 4 to the handle part 2. Thus, the medical probe 1 according to the present invention may prevent the main body 4 from being separated from the handle part 2 since the coupling part 6 couples the main body 4 to the handle part 2. If the coupling part 6 is separated from the insertion groove 41, the main body 4 may be rotated by releasing the coupling from the handle part 2. In this case, the pointing direction of the hook part 5 may be changed. When at least one of the main body 4 or the hook part 5 is damaged, the coupling part 6 may be separated from the insertion groove 41 for maintenance and replacement for the main body 4 and the hook part 5.

The medical probe 1 according to the present invention may further comprise the light hole 7.

The light hole 7 is formed through the handle part 2. The single light hole 7 may be formed in the handle part 2, or there is a plurality of those formed there with spaced apart from each other as well. The light hole 7 may reduce the overall load of the medical probe 1. Accordingly, the operator may easily move the medical prove 1 to the accurate position to treat.

FIG. 7 and FIG. 8 are operation state views which the medical probe 1 according to the present invention indicates the affected area A or B of the patient body P.

Referring FIG. 7 and FIG. 8, a process that the medical probe 1 according to the present invention indicates the affected area A of the patient will be described.

First, the operator initializes the OTS 10 and then the position A where the procedure is planned, is guided on display device.

After that, the operator moves the probe 1 to the planned area A with watching the display device. In this case, the hook part 5 may be located in the planned area A.

After that, it is determined whether the planned area A and the actual position of the probe 1 are same or not. This process may comprise getting the position where the hook part 5 points out with OTS 10 and determining the planned area A and the gotten position are same or not.

After that, if the planned area A and the position of the probe 1 are not same, the operator continues to modify the position by the probe 1 is located at the planned area A. In this case, the pointing direction of the hook part 5 may change depending on the rotation of the main body 4.

After that, if the planned area A and the position of the probe 1 are same, the obtained position is stored. The obtained position may be stored in storage (not shown) installed inside or outside the OTS 10.

Through these processes, the operator may use the obtained position stored in the storage to match a surgical tool in actual surgical procedure with the stored obtained position and thus perform accurate surgical procedure on the affected area A.

The medical probe 1 according to the present invention may obtain a position for the affected area B as well as the affected area A through the same process as described above. Here, with only one incision, the medical probe 1 according to the present invention may obtain a position for the affected area B by rotating the main body 4 as well after obtaining the position of the affected area A. Accordingly, the medical probe 1 according to the present invention can minimize a range of incision area to obtain a wide range of a spatial position information for a procedure thereby reducing the patient's recovery time and obtain quickly the accurate position information for a plurality of affected areas thereby reducing the whole surgical procedure time.

The present invention described above is not limited to the above-described embodiment and the accompanying drawings, and it will be apparent to those skilled in the art that various modifications, substitutions and alterations will be possible without departing from the technical idea of the invention.

What is claimed is:

1. A medical probe comprising:
   a handle part configured to be held by a hand;
   at least one position transmission part coupled to the handle part to reflect or transmit a position signal to an optical tracking system (OTS);
   a main body coupled to one side of the handle part to be positioned at or adjacent to an affected area of a patient; and
   a hook part extended from an end of the main body to touch or indicate the affected area,
   wherein the hook part is connected to the main body to have an angle therebetween,
   wherein the main body is coupled to the handle part to be rotated around a rotation axis with respect to the handle part to change a pointing direction of the hook part,
   wherein the main body includes a first side coupled to the handle part and a second side connected to the first side,
   wherein the first side extends in a first direction different from the rotation axis such that a distal end of the first side is positioned farthest from the rotation axis,
   wherein the second side extends in a second direction different from the first direction such that a distal end of the second side is positioned closer to the rotation axis than the distal end of the first side, the hook part extending from the distal end of the second side, and
   wherein an end of the hook part is positioned on the rotation axis of the main body.

2. The medical probe according to claim 1,
   wherein the hook part is extended in a direction perpendicular to the rotation axis of the main body.

3. The medical probe according to claim 1, further comprising:
   a coupling part configured to couple the main body to the handle part,
   wherein the handle part includes a penetration hole through which the main body is to be inserted,
   wherein the main body includes an insertion groove into which the coupling part is to be inserted, and
   wherein the coupling part is configured to be inserted into the insertion groove to be coupled to the main body so that the main body inserted through the penetration hole is prevented from being separated from the handle part.

4. The medical probe according to claim 3,
   wherein the handle part includes a connection hole formed to be expanded from the penetration hole,
   wherein the main body includes a projection part rotatably coupled to the handle part to be inserted into the connection hole, and
   wherein the projection part has a polygonal shape to fix the main body to the handle part.

5. The medical probe according to claim 1,
   wherein the handle part has a light hole formed therethrough.

6. The medical probe according to claim 1,
wherein the at least one position transmission part includes a plurality of position transmitters coupled to the handle part to be spaced apart each other.

* * * * *